United States Patent [19]

Guigues et al.

[11] 4,297,367

[45] Oct. 27, 1981

[54] 2-PHENYL-4-PYRONE DERIVATIVES, THEIR PREPARATION AND THEIR USE AS FUNGICIDES

[75] Inventors: François Guigues, Rillieux; Stéphane Trinh, Champagne au Mont d'Or, both of France

[73] Assignee: Rhone Poulenc Agrochemie, Lyons, France

[21] Appl. No.: 133,480

[22] Filed: Mar. 24, 1980

[30] Foreign Application Priority Data

Mar. 28, 1979 [FR] France .................................. 79 08569

[51] Int. Cl.³ ..................... A61K 31/35; C07D 309/32
[52] U.S. Cl. ............................. 424/283; 260/345.7 R; 260/345.8 R; 260/465 B; 560/9; 560/22; 560/23; 560/51; 560/53; 564/162; 564/166; 564/167; 564/169
[58] Field of Search .................. 260/345.7 R, 345.8 R; 424/283

[56] References Cited

U.S. PATENT DOCUMENTS 4,060,533 11/1977 Nadelson ..................... 260/345.7 R Primary Examiner—Nicky Chan
Attorney, Agent, or Firm—Robert E. Burns; Emmanuel J. Lobato; Bruce L. Adams

[57] ABSTRACT

The invention relates to new 2-phenyl-4-pyrone derivatives which can be used in agriculture. They correspond to the general formula:

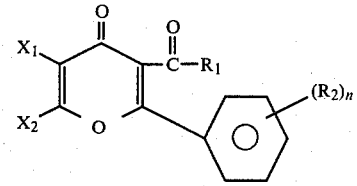

in which $X_1$ and $X_2$, which are identical or different, each represent a hydrogen or halogen atom, with the proviso that at least one of these substituents represents a halogen atom, $R_1$ represents an alkoxy radical ($C_1$–$C_4$), an alkenyloxy radical containing from 2 to 4 carbon atoms, a propargyloxy radical, a halogenoalkoxy radical ($C_1$–$C_4$), an amino radical, an alkylamino radical ($C_1$–$C_4$) or a dialkylamino radical in which each of the alkyl parts, which are identical or different, contains from 1 to 4 carbon atoms, $R_2$ represents a halogen atom, an alkyl radical containing from 1 to 5 carbon atoms, an alkoxy radical ($C_1$–$C_4$), an alkenyloxy radical ($C_3$–$C_4$), an alkynyloxy radical ($C_3$–$C_4$), an alkylthio radical ($C_1$–$C_4$), a halogenoalkyl radical ($C_1$–$C_4$), a halogenoalkoxy radical ($C_1$–$C_4$), a halogenoalkylthio radical ($C_1$–$C_4$) or the nitro, hydroxyl or cyano radical and n is an integer which can be equal to 0, 1, 2, 3, 4 or 5, it being understood that, if n is greater than or equal to 2, the substituents $R_2$ can be identical or different.

They can be used for protecting plants against fungal diseases.

7 Claims, No Drawings

2-PHENYL-4-PYRONE DERIVATIVES, THEIR PREPARATION AND THEIR USE AS FUNGICIDES

The present invention relates to new 2-phenyl-4-pyrone derivatives, their preparation and their use for protecting plants against fungal diseases.

The compounds according to the invention correspond to the general formula (I)

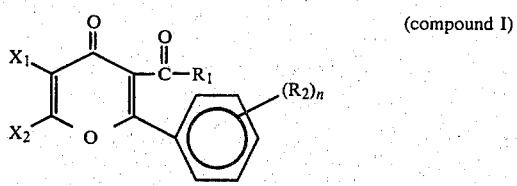
(compound I)

in which $X_1$ and $X_2$, which are idential or different, each represent a hydrogen or halogen atom, with the proviso that at least one of these substituents represents a halogen atom, $R_1$ represents an alkoxy radical containing from 1 to 4 carbon atoms, an alkenyloxy radical containing from 2 to 4 carbon atoms, a propargyloxy radical, a halogenoalkoxy radical containing from 1 to 4 carbon atoms, an amino radical, an alkylamino radical containing from 1 to 4 carbon atoms or a dialkylamino radical in which each of the alkyl parts, which are identical or different, contains from 1 to 4 carbon atoms, $R_2$ represents a halogen atom, an alkyl radical containing from 1 to 5 carbon atoms, an alkoxy radical containing from 1 to 4 carbon atoms, an alkenyloxy radical containing from 3 to 4 carbon atoms, an alkynyloxy radical containing from 3 to 4 carbon atoms, an alkylthio radical containing from 1 to 4 carbon atoms, a halogenoalkyl radical containing from 1 to 4 carbon atoms, a halogenoalkoxy radical containing from 1 to 4 carbon atoms, a halogenoalkylthio radical containing from 1 to 4 carbon atoms or a nitro, hydroxyl, cyano or benzyloxy radical and n is an integer which can be equal to 0, 1, 2, 3, 4 or 5, it being understood that, if n is greater than or equal to 2, the substituents $R_2$ can be identical or different.

Some 2-phenyl-4-pyrone derivatives have already been described in the literature; thus, U.S. Pat. No. 4,060,533 claims, as medicaments having anti-allergic properties, compounds of the formula:

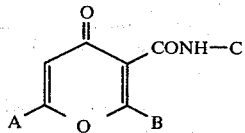

in which A and B each represent a lower alkyl radical or a phenyl radical which is optionally substituted by a halogen atom or a lower alkyl or alkoxy radical and C represents a lower alkyl radical.

The compounds according to the invention are different from those described in this reference. They possess original biological properties, in particular a remarkable fungicidal action against several different species of fungi, and additionally show surprising systemic properties.

A preferred class of compounds according to the invention corresponds to the following formula:

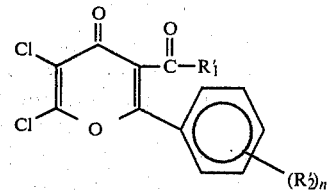

in which $R'_1$ represents an alkoxy radical containing from 1 to 4 carbon atoms, an allyloxy or propargyloxy radical or a dialkylamino radical in which each of the alkyl parts, which are identical or different, contains from 1 to 4 carbon atoms, $R'_2$ represents a halogen atom, an alkyl radical containing from 1 to 4 carbon atoms, an alkoxy radical containing from 1 to 4 carbon atoms or an allyloxy, propargyloxy or trifluoromethyl radical and n' is an integer equal to 1, 2 or 3, it being understood that, if n' is greater than or equal to 2, the radicals $R'_2$ can be identical or different.

The compounds according to the formula I can be prepared in accordance with a process comprising the following successive steps:

STEP A

Reaction of a benzoylacetic acid derivative with a magnesium alcoholate, optionally prepared in situ, in accordance with the equation:

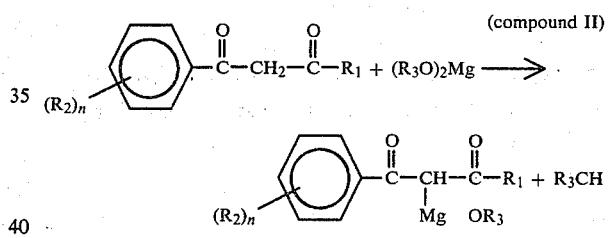
(compound II)

in which $R_1$, $R_2$ and n have the same meaning as in the formula I and $R_3$ represents an alkyl radical containing from 1 to 4 carbon atoms.

The reaction is carried out in an anhydrous medium, advantageously in an inert solvent (i.e. a solvent which does not undergo chemical reaction with the reactants under the operating conditions). The starting reactants are initially brought into contact in the solvent and the reaction mixture thus obtained is then heated at a temperature between about 35° and 150° C. until the reaction is complete. In accordance with an advantageous embodiment, the reaction mixture is heated at the b.p. of the solvent used. Suitable solvents which may be mentioned are polar or non-polar organic solvents, such as aromatic hydrocarbons (e.g. benzene, toluene or xylenes), aliphatic hydrocarbons (e.g. hexane, heptane or cyclohexane) and ethers (e.g. diethyl ether).

Magnesium ethylate is preferably used as the magnesium alcoholate and can be prepared in situ by reacting magnesium with ethanol, in an anhydrous, inert organic solvent, in the presence of carbon tetrachloride.

The benzoylacetic acid derivative, which is the starting material in this step A, is prepared in accordance with the process, described in Organic Syntheses, Volume IV, page 415, for the preparation of ethyl benzoylacetate.

STEP B

Reaction of the chloride of a halogenoacrylic acid with the alkoxymagnesium derivative resulting from step A (compound II), in accordance with the following equation:

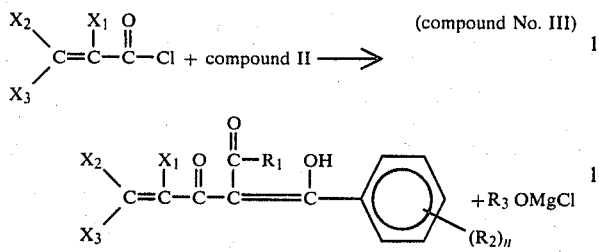

in which $X_1$, $X_2$, $R_1$, $R_2$ and n have the same meaning as in the formula I and $X_3$ represents a halogen atom, preferably chlorine.

The reaction is carried out in an anhydrous medium, advantageously in an inert solvent, at a temperature between about 0° and 40° C.

The solvents mentioned above in respect of step A may be mentioned as solvents which can be used for this second step of the process. It is of course advantageous to use only one solvent and the same solvent for both these steps A and B.

STEP C

Cyclisation of the compound III resulting from the preceding step, to give the compound I in accordance with the equation:

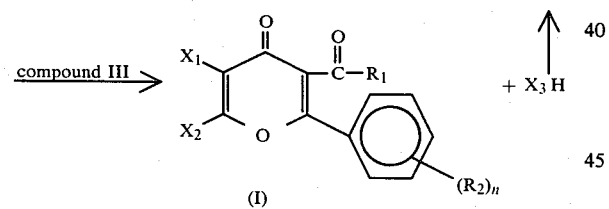

and decomposition, by hydrolysis, of the compound of the formula $R_3OMgCl$ resulting from the preceding step.

This cyclisation is carried out by initially treating the reaction mixture, comprising the compound III and the compound of the formula $R_3OMgCl$, with a dilute aqueous solution of a strong acid, such as sulphuric acid, at a temperature between about 0° and 30° C. (which causes the decomposition of the compound of the formula $R_3OMgCl$ by hydrolysis), and by subsequently heating the organic phase, separated from the aqueous phase beforehand, at a temperature between about 30° and 160° C., optionally under a partial vacuum, so as to evaporate off the solvent and assist the evolution of the hydracid $X_3H$. This heating is continued until the evolution of the hydracid ceases.

The compound of the formula I thus obtained is then purified by the customary methods, such as recrystallisation from a suitable solvent, liquid phase chromatography or the like.

The following examples, which are described without implying a limitation, illustrate the preparation of the compounds according to the invention and also their fungicidal properties.

All the compounds described in these examples were identified by nuclear magnetic resonance spectrometry (NMR). The spectra were run at 60 Megahertz in $CCl_4$ or $CDCl_3$, using hexamethyldisiloxane as the internal standard.

EXAMPLE 1

Preparation of 2-(3-methylphenyl)-3-ethoxycarbonyl-5,6-dichloro-4-pyrone (compound No. 1)

Magnesium ethylate (5.7 g, 0.05 mol) and ethyl m-methylbenzoylacetate (10.3 g, 0.05 mol) are dissolved in toluene (100 ml) at ambient temperature and the solution thus obtained is then heated under reflux for one hour and finally cooled to 5° C. with a bath of iced water.

Trichloroacryloyl chloride (9.7 g) is run dropwise into this solution, kept at a temperature between 0° and 10° C., and the reaction mixture is stirred at ambient temperature for 30 minutes.

The reaction mixture is then poured onto a mixture of ice (100 g) and concentrated sulphuric acid (10 ml). After stirring for one hour, the toluene phase is decanted and the aqueous phase is extracted with toluene (50 ml). The combined toluene phases are washed with water (100 ml), then with a 5% strength solution of sodium bicarbonate (100 ml) and finally with water (100 ml). After drying over anhydrous sodium sulphate and evaporating off the toluene, an oily liquid is obtained which is subsequently heated at 80° C. under a partial vacuum of 16 mm Hg for 30 minutes and then recrystallised from methylcyclohexane (200 ml).

2-(3-Methylphenyl)-3-ethoxycarbonyl-5,6-dichloro-4-pyrone (13 g), which melts at 113° C., is thus obtained with a yield of 79.5%.

| | Elementary composition | |
|---|---|---|
| | Calculated | Found |
| C % | 55.04 | 55.08 |
| H % | 3.67 | 3.58 |
| Cl % | 21.71 | 21.39 |

EXAMPLE 2

Using the appropriate starting materials, compounds Nos. 2 to 44 were prepared by following the method described in the preceding example.

The chemical formulae of these compounds, and also their physico-chemical characteristics, are given in the table below. In the column $R_2$ of this table, the numeral given in front of each of the substituents $R_2$ indicates the position of the particular substituent $R_2$ on the phenyl radical (which is itself in the 2-position on the 4-pyrone ring).

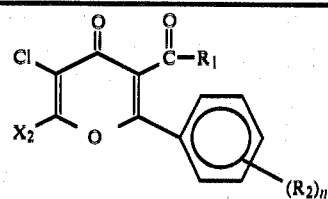

| Compound No. | $X_2$ | $R_1$ | $R_2$ | Empirical formula | M.p. (°C.) | Yield % | | Elementary composition % calculated | % found |
|---|---|---|---|---|---|---|---|---|---|
| 2 | Cl | —OCH$_3$ | 4-F | C$_{13}$H$_7$Cl$_2$FO$_4$ | 107.9 | 66 | C | 49.21 | 50.12 |
| | | | | | | | H | 2.20 | 3.07 |
| | | | | | | | Cl | 22.39 | 22.12 |
| 3 | Cl | —OC$_2$H$_5$ | 4-F | C$_{14}$H$_9$Cl$_2$FO$_4$ | 104.4 | 44 | C | 50.78 | 51.15 |
| | | | | | | | H | 2.74 | 3.27 |
| | | | | | | | Cl | 21.41 | 21.17 |
| 4 | Cl | —OC$_2$H$_5$ | 3-Cl | C$_{14}$H$_9$Cl$_3$O$_4$ | 115 | 78 | C | 48.34 | 48.35 |
| | | | | | | | H | 2.59 | 2.60 |
| | | | | | | | Cl | 30.64 | 30.36 |
| 5 | Cl | —OC$_2$H$_5$ | 4-CH$_3$ | C$_{15}$H$_{12}$Cl$_2$O$_4$ | 112.5 | 73 | C | 55.05 | 55.02 |
| | | | | | | | H | 3.67 | 3.66 |
| | | | | | | | Cl | 21.71 | 21.67 |
| 6 | Cl | —OC$_2$H$_5$ | 4-C$_2$H$_5$ | C$_{16}$H$_{14}$Cl$_2$O$_4$ | 70.5 | 71 | C | 56.30 | 56.36 |
| | | | | | | | H | 4.11 | 4.24 |
| | | | | | | | Cl | 20.82 | 20.46 |
| 7 | Cl | —OC$_2$H$_5$ | 4-CH(CH$_3$)$_2$ | C$_{17}$H$_{16}$Cl$_2$O$_4$ | 100.5 | 66.8 | C | 57.48 | 57.67 |
| | | | | | | | H | 4.54 | 4.76 |
| | | | | | | | Cl | 19.96 | 19.86 |
| 8 | Cl | —OC$_2$H$_5$ | 4-CH(CH$_2$—CH$_3$)(CH$_3$) | C$_{18}$H$_{18}$Cl$_2$O$_4$ | 64 | 21 | C | 58.54 | 58.39 |
| | | | | | | | H | 4.88 | 4.83 |
| | | | | | | | Cl | 19.24 | 18.52 |
| 9 | Cl | —OC$_2$H$_5$ | 4-C(CH$_3$)$_3$ | C$_{18}$H$_{18}$Cl$_2$O$_4$ | 131.5 | 66 | C | 58.53 | 58.54 |
| | | | | | | | H | 4.88 | 4.91 |
| | | | | | | | Cl | 19.24 | 18.93 |
| 10 | Cl | —OC$_2$H$_5$ | 2-OCH$_3$ | C$_{15}$H$_{12}$Cl$_2$O$_5$ | 135 | 53 | C | 52.47 | 52.51 |
| | | | | | | | H | 3.49 | 3.63 |
| | | | | | | | Cl | 20.70 | 20.46 |
| 11 | Cl | —OC$_2$H$_5$ | 3-CF$_3$ | C$_{15}$H$_9$Cl$_2$F$_3$O$_4$ | 113 | 67 | C | 47.24 | 46.43 |
| | | | | | | | H | 2.36 | 2.42 |
| | | | | | | | Cl | 18.37 | 18.59 |
| 12 | Cl | —OC$_2$H$_5$ | 3-CH$_3$ 4-F | C$_{15}$H$_{11}$Cl$_2$FO$_4$ | 124 | 70 | C | 52.17 | 52.12 |
| | | | | | | | H | 3.18 | 3.23 |
| | | | | | | | Cl | 20.58 | 20.66 |
| 13 | Cl | —OC$_2$H$_5$ | 3-CH(CH$_3$)$_2$ 4-F | C$_{17}$H$_{15}$Cl$_2$FO$_4$ | 116 | 65 | C | 54.79 | 54.59 |
| | | | | | | | H | 4.02 | 4.16 |
| | | | | | | | Cl | 19.03 | 19.10 |
| 14 | Cl | —OC$_2$H$_5$ | 3-CH$_3$ 4-CH$_3$ | C$_{16}$H$_{14}$Cl$_2$O$_4$ | 151.5 | 70 | C | 56.30 | 56.28 |
| | | | | | | | H | 4.10 | 4.02 |
| | | | | | | | Cl | 20.82 | 20.75 |
| 15 | Cl | —OC$_2$H$_5$ | 3-OCH$_3$ 4-OCH$_3$ | C$_{16}$H$_{14}$Cl$_2$O$_6$ | 132.5 | 68 | C | 51.47 | 51.58 |
| | | | | | | | H | 3.75 | 3.85 |
| | | | | | | | Cl | 19.03 | 19.12 |
| 16 | Cl | —OC$_2$H$_5$ | 3-CH$_3$ 4-OCH$_3$ 6-CH$_3$ | C$_{17}$H$_{16}$Cl$_2$O$_5$ | 129 | 83 | C | 54.98 | 54.98 |
| | | | | | | | H | 4.31 | 4.49 |
| | | | | | | | Cl | 19.13 | 18.92 |
| 17 | Cl | —OC$_2$H$_5$ | 3-OCH$_3$ 4-OCH$_3$ 5-OCH$_3$ | C$_{17}$H$_{16}$Cl$_2$O$_7$ | 131 | 57 | C | 50.62 | 50.57 |
| | | | | | | | H | 3.97 | 3.86 |
| | | | | | | | Cl | 17.60 | 17.35 |
| 18 | Cl | —O(CH$_2$)$_2$—CH$_3$ | 4-CH(CH$_3$)$_2$ | C$_{18}$H$_{18}$Cl$_2$O$_4$ | 58.9 | 38 | C | 58.55 | 58.71 |
| | | | | | | | H | 4.91 | 5.03 |
| | | | | | | | Cl | 19.20 | 18.84 |
| 19 | Cl | —OCH(CH$_3$)$_2$ | 4-CH$_3$ | C$_{16}$H$_{14}$Cl$_2$O$_4$ | 80 | 74 | C | 56.30 | 56.51 |
| | | | | | | | H | 4.11 | 4.27 |
| | | | | | | | Cl | 20.82 | 20.71 |
| 20 | Cl | —OCH(CH$_3$)$_2$ | 4-C(CH$_3$)$_3$ | C$_{19}$H$_{20}$Cl$_2$O$_4$ | 106 | 70.5 | C | 59.53 | 59.66 |
| | | | | | | | H | 5.22 | 5.33 |
| | | | | | | | Cl | 18.54 | 18.28 |
| 21 | Cl | —OCH(CH$_3$)$_2$ | 4-F | C$_{15}$H$_{11}$Cl$_2$FO$_4$ | 97.5 | 81 | C | 52.20 | 52.90 |
| | | | | | | | H | 3.20 | 3.07 |
| | | | | | | | Cl | 20.68 | 20.65 |
| 22 | Cl | —OCH$_2$—CH=CH$_2$ | 4-C(CH$_3$)$_3$ | C$_{19}$H$_{18}$Cl$_2$O$_4$ | 72.7 | 61.5 | C | 59.84 | 59.72 |
| | | | | | | | H | 4.72 | 4.99 |
| | | | | | | | Cl | 18.64 | 18.49 |
| 23 | Cl | —OCH$_2$—C≡CH | 4-F | C$_{15}$H$_7$Cl$_2$FO$_4$ | 121.5 | 60 | C | 52.78 | 52.75 |
| | | | | | | | H | 2.05 | 2.00 |
| | | | | | | | Cl | 20.82 | 20.70 |
| 24 | Cl | —O—CH$_2$—CH$_2$—Cl | 4-F | C$_{14}$H$_8$Cl$_3$FO$_4$ | 115.5 | 36.5 | C | 45.96 | 46.81 |

-continued

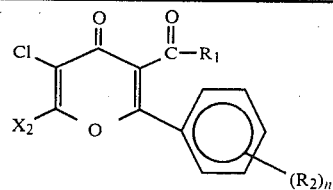

| Compound No. | $X_2$ | $R_1$ | $R_2$ | Empirical formula | M.p. (°C.) | Yield % | Elementary composition | % calculated | % found |
|---|---|---|---|---|---|---|---|---|---|
| 25 | Cl | $-N(C_2H_5)_2$ | 4-F | $C_{16}H_{14}Cl_2FNO_3$ | 123.5 | 56 | H<br>Cl<br>C<br>H<br>N | 2.19<br>29.10<br>53.63<br>3.91<br>3.91 | 2.45<br>29.60<br>53.65<br>3.92<br>3.97 |
| 26 | H | $-OC_2H_5$ | 4-F | $C_{14}H_{10}ClFO_4$ | 85.0 | 40 | | | |
| 27 | Cl | $OC_2H_5$ | 3-$CH_3$ | $C_{15}H_{12}Cl_2O_4$ | 113 | 80.0 | C<br>H<br>Cl | 55.05<br>3.67<br>21.71 | 55.04<br>3.55<br>21.47 |
| 28 | Cl | $O-C(CH_3)_3$ | 4-F | $C_{16}H_{13}Cl_2FO_4$ | 109 | 50.1 | C<br>H<br>Cl | 53.50<br>3.60<br>19.80 | 53.74<br>3.73<br>19.74 |
| 29 | Cl | $OC_2H_5$ | 3-Cl<br>4-F | $C_{14}H_8Cl_3FO_4$ | 140.3 | 63.9 | C<br>H<br>Cl | 45.96<br>2.19<br>29.14 | 46.08<br>2.22<br>28.95 |
| 30 | Cl | $OC_2H_5$ | 2-$CF_3$ | $C_{15}H_9Cl_2F_3O_4$ | 82.5 | 65.6 | C<br>H<br>Cl | 47.24<br>2.36<br>18.64 | 47.12<br>2.50<br>17.84 |
| 31 | Cl | $OC_2H_5$ | 2-Cl | $C_{14}H_9Cl_3O_4$ | 126.8 | 58.5 | C<br>H<br>Cl | 48.34<br>2.59<br>30.64 | 47.82<br>2.68<br>30.33 |
| 32 | Cl | $OC_2H_5$ | 4-Cl | $C_{14}H_9Cl_3O_4$ | 111.6 | 48.9 | C<br>H<br>Cl | 48.34<br>2.59<br>30.65 | 48.69<br>2.76<br>30.22 |
| 33 | Cl | $OC_2H_5$ | 3-Br | $C_{14}H_9BrCl_2O_4$ | 120.5 | 68.0 | C<br>H<br>Br<br>Cl | 42.86<br>2.29<br>20.41<br>18.11 | 42.52<br>2.28<br>19.93<br>17.39 |
| 34 | Cl | $OC_2H_5$ | 4-Br | $C_{14}H_9BrCl_2O_4$ | 112.7 | 66.3 | C<br>H<br>Br<br>Cl | 42.86<br>2.29<br>20.41<br>18.11 | 43.37<br>2.55<br>19.70<br>18.08 |
| 35 | Cl | $OC_2H_5$ | 3-F | $C_{14}H_9Cl_2O_4$ | 104.0 | 67.3 | C<br>H<br>Cl | 50.75<br>2.72<br>21.45 | 50.92<br>2.72<br>21.38 |
| 36 | Cl | $OC_2H_5$ | 3-Cl<br>5-Cl | $C_{14}H_8Cl_4O_4$ | 128.1 | 70.7 | C<br>H<br>Cl | 43.98<br>2.09<br>37.17 | 44.36<br>2.54<br>36.68 |
| 37 | Cl | $OC_2H_5$ | 2-Cl<br>4-Cl | $C_{14}H_8Cl_4O_4$ | 92.5 | 57.6 | C<br>H<br>Cl | 43.98<br>2.09<br>37.17 | 43.85<br>2.23<br>36.43 |
| 38 | Cl | $OC_2H_5$ | 2-Cl<br>3-Cl<br>5-Cl | $C_{14}H_7Cl_5O_4$ | 176.4 | 44.3 | C<br>H<br>Cl | 40.34<br>1.68<br>42.62 | 40.82<br>2.00<br>41.90 |
| 39 | Cl | $OC_2H_5$ | 4-$NO_2$ | $C_{14}H_9Cl_2NO_6$ | 123.6 | 49.5 | C<br>H<br>N<br>Cl | 46.93<br>2.51<br>3.91<br>19.83 | 46.27<br>2.48<br>3.95<br>19.93 |
| 40 | Cl | $OC_2H_5$ | 4-$CF_3$ | $C_{15}H_9Cl_2F_3O_4$ | 68.5 | 44.6 | C<br>H<br>Cl | 47.24<br>2.36<br>18.63 | 47.39<br>2.26<br>18.77 |
| 41 | Cl | $OC_2H_5$ | 4-$OC_2H_5$ | $C_{16}H_{14}Cl_2O_5$ | 115.5 | 51.0 | C<br>H<br>Cl | 53.78<br>3.92<br>19.89 | 53.59<br>3.82<br>19.69 |
| 42 | Cl | $OC_2H_5$ | 4-O-$CH_2$-$C_6H_5$ | $C_{21}H_{16}Cl_2O_5$ | 119.8 | 47.0 | C<br>H<br>Cl | 60.14<br>3.82<br>16.94 | 59.97<br>3.76<br>16.39 |
| 43 | Cl | $OC_2H_5$ | 4-$OCH_2CH=CH_2$ | $C_{17}H_{14}Cl_2O_5$ | 108.8 | 35.8 | C<br>H<br>Cl | 55.28<br>3.79<br>19.24 | 56.01<br>3.76<br>19.41 |
| 44 | Cl | $OC_2H_5$ | 4-$OCH_2-C\equiv CH$ | $C_{17}H_{12}Cl_2O_5$ | 95.6 | 23.3 | C<br>H<br>Cl | 55.58<br>3.26<br>19.35 | 55.03<br>3.18<br>18.56 |

EXAMPLE 3

In vitro test for the anti-fungal activity of the compounds according to the invention The action of the compounds according to the invention against the following fungus: *Piricularia oryzae*, which is responsible for piriculariose in rice, is studied.

For each experiment, the procedure is as follows: gelose (malt/agar medium) (5 ml) is placed in test tubes and each tube is then stoppered and sterilised for 20 minutes at 120° C. The tubes are then placed in a waterbath kept at 60° C. A defined amount of a 1% strength acetone solution of the compound to be tested is then injected into each tube with the aid of a pipette, so as to obtain a defined concentration of this compound in the culture. After 24 hours, the tubes are inoculated by injection, using a syringe, with a suspension of spores containing about 100,000 spores/ml (0.5 ml). A tube which is analogous to the above but in which the gelose medium does not contain any active ingredient is taken as the control. The tubes are kept in the dark for 7 days, at 26° C., and the growth of the fungus in the tubes containing the active ingredient to be tested is then compared with that of the untreated control. For each of the compounds tested, the lowest dose which makes it possible totally to inhibit the development of the fungus in question is thus determined. This dose is respectively:

0.2 g/liter for compounds Nos. 14, 15, 18, 26 and 38,
0.1 g/liter for compounds Nos. 39, 41 and 42, and
0.05 g/liter for compounds Nos. 1, 3, 6, 9, 10, 11, 12, 17, 19, 27, 28, 29, 31, 32, 33, 34, 36, 37 and 40.

It is equal to or less than 0.01 g/liter for compounds Nos. 2, 4, 5, 7, 8, 13, 16, 20, 21, 22, 23, 30, 35, 43 and 44.

EXAMPLE 4

In vivo test using *Plasmopara viticola* on vine plants (preventive treatment)

Vine plants (Gamay variety), cultivated in pots, are treated by spraying the underside of the leaves, using a gun, with an aqueous suspension of a wettable powder having the following composition by weight:

| | |
|---|---|
| active ingredient to be tested | 20% |
| deflocculant (calcium lignosulphonate) | 5% |
| wetting agent (sodium alkylarylsulphonate) | 1% |
| filler (aluminum silicate) | 74% | the suspension being at the desired dilution which contains the active ingredient to be tested, at the relevant dose. Each test is repeated three times.

After 48 hours, contamination is carried out by spraying the underside of the leaves with an aqueous suspension containing about 80,000 units/cc of spores of *Plasmopara viticola*, which is responsible for vine mildew. The pots are then placed for 48 hours in an incubation cell at 100% relative humidity and at 20° C.

The plants are checked 9 days after infestation.

Under these conditions, it is observed that a total protection (>95%) is achieved at the following doses in the case of the compounds mentioned below:

0.015 g/liter: compound No. 34,
0.06 g/liter: compounds Nos. 1 and 35,
0.12 g/liter: compounds Nos. 31 and 41, and
0.25 g/liter: compounds Nos. , 11, 18, 23, 33, 36, 37, 38, 39 and 40.

At this same dose of 0.25 g/liter, compounds Nos. 2, 3, 4, 5, 10, 12, 13, 15, 16 and 17 effect a good protection (from 75 to 95%). Furthermore, no phytotoxicity phenomenon was observed in this experiment.

EXAMPLE 5

In vivo test using "Uromyces phaseoli", which is responsible for bean rust (preventive treatment)

Bean plants are cultivated in pots of diameter 8 cm, which are filled with peat. At the two cotyledonary leaf stage, the plants are treated by spraying them with an aqueous suspension of the same wettable powder as in Example 4, the suspension containing the product to be tested, at the desired dose.

After 48 hours, the beans are sprayed with a suspension of spores (50,000 spores/cc), obtained from contaminated plants. The beans are subsequently placed firstly in an incubation cell at 100% relative humidity and 20° C., for 48 hours, and then in a greenhouse under the following conditions:

| | |
|---|---|
| Day temperature | 20° C.–25° C. |
| Night temperature | 15° C.–20° C. |
| Relative humidity | 70 to 80% |

The plants are checked 15 days after contamination and compared with the untreated control. Under these conditions, it is observed that, at a dose of 0.50 g/liter, compounds Nos. 11, 27, 30, 31, 35, 36 and 40 effect a total protection (>95%) and compounds Nos. 3 and 4 effect a good protection (from 75 to 95%).

EXAMPLE 6

In vivo test using "Puccinia striiformis", which is responsible for yellow rust in cereals (preventive treatment)

Wheat grains of the "Joss" variety are sown in pots of diameter 8 cm. Eight days after sowing, the wheat plants are treated by spraying them with an aqueous suspension of a wettable powder having the following composition by weight:

| | |
|---|---|
| 2-(4-fluorophenyl)-3-ethoxycarbonyl-5,6-dichloro-4-pyrone (compound no. 3) | 20% |
| calcium lignosulphonate | 5% |
| alkylarylsulphonate | 1% |
| aluminum silicate | 74% |

The treatment is carried out for various concentrations of active ingredient in the aqueous suspension, each test being repeated three times.

48 hours after the treatment, the wheat is sprayed with a suspension of spores (50,000 spores/ml), obtained from contaminated plants. The wheat is then placed in an incubation cell regulated as in Example 5. The plants are checked 15 days after contamination and compared with an untreated control. Under these conditions, it is observed that, at doses of 0.5 g/liter, 0.250 g/liter and 0.125 g/liter, compound No. 3 effects a good protection (from 75 to 95%). During this experiment, no phenomenon of phytotoxicity towards the treated plants was observed.

EXAMPLE 7

Field test using "Puccinia recondita", which is responsible for brown rust in cereals Wheat grains of the "Nebraska" variety are sown in the autumn in plots of 50 m² each. On 10th May of the following year, the wheat plants are treated by spraying them with a mixture obtained by diluting, with water, a wettable powder having the following composition by weight:

| | |
|---|---|
| active ingredient to be tested | 500 |
| wetting agent (sodium alkylarylsulphonate) | 10 |
| deflocculant (calcium lignosulphonate) | 50 |
| anti-caking silica | 50 |
| filler (kaolinite) | 390 |

This mixture contains 200 g/hectoliter of active ingredient and is applied by spraying at a rate of 500 liters/hectare, which corresponds to a dose of 1,000 g/hectare of active ingredient, each test being repeated 4 times. Towards the end of May, the appearance of contamination by brown rust is observed. A second treatment is carried out on 7th June using, for each of the plots, the same conditions as in the treatment of 10th May.

The plants are checked on 12th July and the leaf surface covered by pustules of brown rust is then evaluated (in %) and compared with the results observed in the case of an untreated control plot; under these conditions, it is observed that this % is 1.9%, on average, in the case of the plots treated with the composition containing compound No. 3 and 35.7% in the case of the control plots.

EXAMPLE 8

Field test using "Venturia inequalis", which is responsible for apple scab

Plots of 30 m² each, which contain 5 apple trees of the "golden delicious" variety per plot, are treated on 15th March, when the disease appears, with a mixture obtained by diluting, with water, the same composition as in Example 7. This mixture contains 100 g/hectoliter of active ingredient (compound no. 3) and is applied by spraying at a rate of 1,000 liters/hectare, which corresponds to a dose of 1 kg/hectare of active ingredient.

Other plots are treated on the same day with a mixture which contains 150 g/liter of captane and is applied at a rate of 1,000 liters/hectare, which corresponds to 1.5 kg/hectare of captan. These treatments are repeated every 15 days, under the same conditions, up to a total of 6 treatments for each of the active ingredients applied. Each test is repeated 4 times. Some plots are left untreated to be used as a control.

The trees are checked on 20th June and the % of diseased leaves and the % of the surface of the leaves which has been contaminated are then determined.

| | dose kg/ hectare | number of treatments | % of diseased leaves | % of the surface contaminated |
|---|---|---|---|---|
| compound No. 3 | 1 | 6 | 0.3 | 0.01 |
| captan | 1.5 | 6 | 1.3 | 0.1 |
| control | 0 | — | 69.8 | 18.6 |

EXAMPLE 9

Field test using "Septoria apii", which is responsible for leaf spot in celery

Celery plants of the "Gennevilliers" variety are transplanted on 6th June into plots of 2 m² and a plant contaminated by the disease is transplanted into each of these plots on 1st July.

Treatments are carried out on 7th August and 23rd August using a mixture prepared by diluting, with water, the same composition as in Example 7. This mixture contains 100 g/hectoliter of active ingredient and is applied by spraying at a rate of 1,000 liters/hectare, which corresponds to a dose of 1 kg/hectare of active ingredient.

Other plots are treated on the same days with maneb at a rate of 2.4 kg/hectare of active ingredient for each treatment. Some plots are left untreated to be used as a control.

The plants are checked on 29th August and the % of the surface of the leaves which has been contaminted is then determined.

| | dose kg/ hectare | number of treatments | % of the surface contaminated |
|---|---|---|---|
| compound No. 3 | 1 | 2 | 19.1 |
| maneb | 2.4 | 2 | 24.0 |
| control | | | 60.0 |

The above examples clearly illustrate the remarkable anti-fungal properties of the compounds according to the invention on various species of fungi, such as Basidiomycetes (in particular *Puccinia striiformis, Puccinia recondita* and *Uromyces phaseoli*), Ascomycetes (in particular *Venturia inequalis*), Fungi imperfecti (in particular *Piricularia orizae* and *Septoria apii*) and Phycomycetes (in particular *Plasmopara viticola*), and also their lack of action against the crops in question.

Excellent results have also been observed in respect of several seed fungi, such as *Fusarium nivale* and *Fusarium culmorum*.

Particularly advantageous results have been observed in the case of the following compounds: 2-(4-fluorophenyl)-3-ethoxycarbonyl-5,6-dichloro-4-pyrone (compound No. 3) and 2-(3-trifluoromethylphenyl)-3-ethoxycarbonyl-5,6-dichloro-4-pyrone (compound No. 11).

The use doses can vary within wide limits, depending on the virulence of the fungus and the climatic conditions. In general terms, compositions containing from 0.01 to 5 g/liter of active ingredient are suitable.

For their use in practice, the compounds according to the invention are rarely employed by themselves. Most frequently, they form part of compositions which also fall within the scope of the invention and which generally comprise, in addition to the active ingredient, a carrier and, if appropriate, a surface-active agent. The proportion of active ingredient in these compositions is generally beteween 0.0005 and 95% by weight.

The term "carrier", for the purpose of the present description, denotes an organic or inorganic, natural or synthetic material with which the active ingredient is combined in order to facilitate its application to the plant, to the seeds or to the soil, or in order to facilitate its transportation or handling. This carrier must therefore be inert and acceptable in agriculture, in particular to the plant. The carrier can be solid (clays, natural or synthetic silicates, resins, waxes, solid fertilisers or the like) or liquid (water, alcohols, ketones, petroleum fractions, chlorohydrocarbons, aromatic or paraffinic hydrocarbons, liquefied gases or the like).

The surface-active agent can be an emulsifying, dispersing or wetting agent of the ionic or non-ionic type. Examples which may be mentioned are salts of polyacrylic acids, salts of lignosulphonic acids, salts of phenolsulphonic or naphthalenesulphonic acids, products resulting from the polycondensation of ethylene oxide with fatty alcohols, fatty acids or fatty amines, substituted phenols (in particular alkylphenols or arylphenols), salts of sulphosuccinic acid esters, and phosphoric acid esters of polyoxyethyleneated alcohols or phenols.

These compositions can also contain any other kinds of ingredients, such as e.g. protective colloids, adhesives, thickeners, penetrating agents, stabilisers, sequestering agents and the like, and also any other kinds of known active ingredients which have pesticidal properties (in particular insecticidal or fungicidal properties) or which promote the growth of plants (in particular fertilisers).

The compositions according to the invention can be prepared in the form of wettable powders, soluble powders, dusting powders, solutions, emulsifiable concentrates, emulsions, suspension concentrates and aerosols.

The wettable powders are usually prepared so that they contain from 20 to 95% by weight of active ingredient, and they usually contain, in addition to the solid carrier, from 0 to 5% by weight of a wetting agent, from 3 to 10% by weight of a dispersing agent and, if necessary, from 0 to 10% by weight of one or more stabilisers and/or other additives, such as penetrating agents, adhesives or anti-caking agents, dyestuffs and the like. The composition by weight of a wettable powder according to the invention is given below by way of example:

| active ingredient (compound No. 3) | 500 g |
|---|---|
| calcium lignosulphonate (deflocculant) | 50 g |
| isopropylnaphthalenesulphonate (anionic wetting agent) | 10 g |
| anti-caking silica | 50 g |
| kaolin | 390 g |

Another example of a wettable powder according to the invention has the following composition by weight:

| active ingredient (compound No. 1) | 700 g |
|---|---|
| sodium dibutylnaphthylsulphonate | 50 g |
| product resulting from the condensation of naphthalenesulphonic acid, phenolsulphonic acid and formaldehyde in proportions of 3/2/1 | 30 g |
| kaolin | 100 g |
| Champagne chalk | 120 g |

A third example of a wettable powder according to the invention has the following composition by weight:

| active ingredient | 250 g |
|---|---|
| calcium lignosulphonate | 45 g |
| mixture of equal weights of Champagne chalk and hydroxyethylcellulose | 19 g |
| sodium dibutylnaphthalenesulphonate | 15 g |
| silica | 195 g |
| Champagne chalk | 195 g |
| kaolin | 281 g |

The compounds according to the invention can also be used in the form of dusting powders having e.g. the following composition by weight:

| active ingredient | 50 g |
|---|---|
| talc | 950 g |

The emulsifiable concentrates, which can be applied by spraying, usually contain from 10 to 50% by weight/volume of active ingredient, from 2 to 20% weight/volume of an emulsifying agent, and, where necessary, from 2 to 20% by weight/volume of suitable additives, such as surface-active agents, stabilisers, penetrating agents, corrosion inhibitors, dyestuffs and adhesives. The composition of an emulsifiable concentrate is given below by way of example, the amounts being expressed in g/liter:

| active ingredient (compound No. 3) | 400 g/liter |
|---|---|
| alkali metal dodecylbenzenesulphonate | 24 g/liter |
| oxyethyleneated nonylphenol containing 10 molecules of ethylene oxide | 16 g/liter |
| cyclohexanone | 200 g/liter |
| aromatic solvent q.s.p. | 1 liter |

The suspension concentrates, which can also be applied by spraying, are prepared so as to give a stable fluid product which does not form a deposit, and they usually contain from 10 to 75% by weight of active ingredient, from 0.5 to 15% by weight of surface-active agents, from 0.1 to 10% by weight of thixotropic agents, from 0 to 10% of suitable additives, such as anti-foam agents, corrosion inhibitors, stabilisers, penetrating agents and adhesives, and, as the carrier, water or an organic liquid in which the active ingredient is essentially insoluble; certain organic solids or inorganic salts, can be dissolved in the carrier in order to prevent sedimentation or to act as anti-freeze agents for the water.

Aqueous dispersions and aqueous emulsions, which are obtained by diluting, with water, compositions mentioned above, in particular the wettable powders and emulsifiable concentrates according to the invention, also fall within the general scope of the present invention. The emulsions thus obtained can be of the water-in-oil type or of the oil-in-water type and they can have a thick consistency such as that of a mayonnaise.

We claim:

1. A 2-phenyl-4-pyrone derivative of the formula

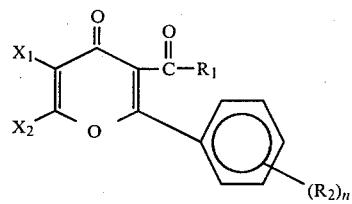

in which $X_1$ and $X_2$, which are identical or different, each represent a hydrogen or halogen atom, with the proviso that at least one of these substituents represents a halogen atom, $R_1$ represents an alkoxy radical containing from 1 to 4 carbon atoms, an alkenyloxy radical containing from 2 to 4 carbon atoms, the propargyloxy radical, a halogenoalkoxy radical containing from 1 to 4 carbon atoms, an amino radical, an alkylamino radical containing from 1 to 4 carbon atoms or a dialkylamino radical in which the alkyl groups containing from 1 to 4 carbon atoms are identical or different, $R_2$ represents a halogen atom, an alkyl radical containing from 1 to 5 carbon atoms, an alkoxy radical containing from 1 to 4 carbon atoms, an alkenyloxy radical containing from 3 to 4 carbon atoms, an alkynyloxy radical containing from 3 to 4 carbon atoms, an alkylthio radical containing from 1 to 4 carbon atoms, a halogenoalkyl radical containing from 1 to 4 carbon atoms, a halogenoalkoxy radical containing from 1 to 4 carbon atoms, a halogenoalkylthio radical containing from 1 to 4 carbon atoms or a nitro, hydroxyl, cyano or benzyloxy radical and n is an integer which can be equal to 0, 1, 2, 3, 4 or 5, it being understood that, if n is greater than or equal to 2, the substituents $R_2$ can be identical or different.

2. A compound according to claim 1, of the formula:

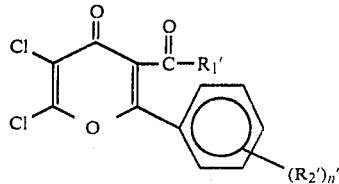

in which $R'_1$ represents an alkoxy radical containing from 1 to 4 carbon atoms, an allyloxy or propargyloxy radical or a dialkylamino radical in which each of the alkyl parts, which are identical or different, contains from 1 to 4 carbon atoms, $R'_2$ represents a halogen atom, an alkyl radical containing from 1 to 4 carbon atoms, an alkoxy radical containing from 1 to 4 carbon atoms, an allyloxy or propargyloxy radical or the trifluoromethyl radical and n' is an integer equal to 1, 2 or 3, it being understood that, if n' is greater than or equal to 2, the radicals $R'_2$ can be identical or different.

3. A compound according to claim 1, which is 2-(4-fluorophenyl)-3-ethoxycarbonyl-5,6-dichloro-4-pyrone.

4. A compound according to claim 1, which is 2-(3-trifluoromethylphenyl)-3-ethoxycarbonyl-5,6-dichloro-4-pyrone.

5. A composition for protecting plants against fungal diseases, which contains an effective amount of at least one compound according to claim 1, in association with a carrier and/or a surface-active agent which can be used in agriculture and are compatible with the said active ingredient.

6. A composition according to claim 5, which contains from 0.01 to 95% by weight of active ingredient.

7. A process for treating plants against fungal diseases, which comprises using a composition according to one of claims 5 to 6.

* * * * *